(12) United States Patent
Rasmussen et al.

(10) Patent No.: US 8,480,725 B2
(45) Date of Patent: Jul. 9, 2013

(54) INTRODUCER FOR DEPLOYING A STENT GRAFT IN A CURVED LUMEN

(75) Inventors: Erik Rasmussen, Slagelse (DK); Bent Øhlenschlaeger, Li. Skensved (DK); Kim Moegelvang Jensen, Koebenhavn (DK)

(73) Assignee: Cook Medical Technologies LLC, Bloomington, IN (US)

( * ) Notice: Subject to any disclaimer, the term of this patent is extended or adjusted under 35 U.S.C. 154(b) by 185 days.

(21) Appl. No.: 12/609,553

(22) Filed: Oct. 30, 2009

(65) Prior Publication Data

US 2010/0114290 A1    May 6, 2010

(30) Foreign Application Priority Data

Oct. 31, 2008    (GB) .................................. 0820066.9

(51) Int. Cl.
*A61F 2/06*        (2006.01)
(52) U.S. Cl.
USPC ........................................................ 623/1.12
(58) Field of Classification Search
USPC ................. 623/1.11, 1.12, 1.13, 1.15, 1.16, 623/1.23
See application file for complete search history.

(56) References Cited

U.S. PATENT DOCUMENTS

| | | | |
|---|---|---|---|
| 6,346,118 B1 * | 2/2002 | Baker et al. ................... | 623/1.12 |
| 6,350,277 B1 * | 2/2002 | Kocur ........................... | 623/1.11 |
| 6,514,282 B1 * | 2/2003 | Inoue ............................ | 623/1.13 |
| 6,974,471 B2 | 12/2005 | Van Schie et al. | |
| 7,279,003 B2 | 10/2007 | Berra et al. | |
| 7,318,835 B2 | 1/2008 | Berra | |
| 2004/0073289 A1 | 4/2004 | Hartley | |
| 2004/0106978 A1 * | 6/2004 | Greenberg et al. .......... | 623/1.13 |
| 2005/0119722 A1 * | 6/2005 | Styrc et al. ................... | 623/1.12 |
| 2005/0240257 A1 * | 10/2005 | Ishimaru et al. ............. | 623/1.15 |
| 2006/0190070 A1 * | 8/2006 | Dieck et al. .................. | 623/1.12 |
| 2007/0043425 A1 * | 2/2007 | Hartley et al. ................ | 623/1.12 |

FOREIGN PATENT DOCUMENTS

| | | |
|---|---|---|
| WO | WO 03/034948 | 5/2003 |
| WO | WO 2004/017868 | 3/2004 |
| WO | WO 2008/051543 | 5/2008 |

* cited by examiner

*Primary Examiner* — Gary Jackson
*Assistant Examiner* — Jonathan Hollm
(74) *Attorney, Agent, or Firm* — Brinks Hofer Gilson & Lione (57) ABSTRACT

An introducer (10) includes release wires (42') that constrain at least one stent (4') while the remainder of a stent graft (18) is expanded during deployment. By allowing the constrained stent (4') to expand after an adjacent stent (4), the constrained stent (4') overlaps with the interior of the adjacent stent (4) where the stent graft (18) is deployed within a curved body lumen (70).

8 Claims, 9 Drawing Sheets

INTRODUCER FOR DEPLOYING A STENT GRAFT IN A CURVED LUMEN

CROSS-REFERENCE TO RELATED APPLICATIONS

This application claims priority of United Kingdom patent application number, 0820066.9, filed Oct. 31, 2008. This application is related to United Kingdom patent application number 0820061.0, filed Oct. 31, 2008.

TECHNICAL FIELD

The present invention relates to an introducer for deploying a stent graft within a curved lumen.

BACKGROUND OF THE INVENTION

Stent grafts are used to replace or repair vessels of the body such as the arteries. A stent graft is usually formed from a tubular body of a biocompatible graft with one or more stents mounted into or onto the tubular body to provide support therefor. The stents may be balloon expandable stents or self-expanding stents.

Endovascular methods have been proposed for treatment of an aneurysm of the aorta particularly where the aneurysm is adjacent the aorta bifurcation. However, when an aneurysm occurs higher up in the aorta, in the region of the descending aorta adjacent the thoracic arch or in the ascending aorta, endovascular techniques for treating these aneurysms are somewhat more difficult because of the tight curvature of the thoracic arch, the occurrence of major arteries in the region and the proximity to the heart. Placement of a substantially cylindrical prosthesis in such a curved region can cause problems.

Stent grafts are typically deployed using endovascular techniques on an introduction device in which the stent graft is retained in a radially contracted condition by a sheath. Upon withdrawal of the sheath and release of any retention arrangement where provided, for example in cases in which the stent graft has self-expanding stents, the stent graft can expand under the action of the self-expanding stents towards the vessel walls to redefine the blood flow path. The introduction device is withdrawn after deployment.

Currently, stent grafts are deployed in curved lumens by causing these to follow the curvature imparted to the introducer. However, this can result in the stent graft not sitting properly in the blood vessel and in the lumen of the prosthesis being closed off or reduced in diameter. Kinks can also occur along the length of the prosthesis and these can cause problems with restriction of flow in the lumen.

Furthermore, when deploying a stent graft that is substantially cylindrical in a curved aorta there is a danger that the proximal end of the stent graft, that is, the end nearest the heart, will not lie flat against the walls of the aorta (i.e., is not positioned perpendicularly to the wall of the vessel) and blood can flow underneath the edge of the graft, particularly on the inner side of the curve of the thoracic arch and cause the stent graft to buckle and close off thereby causing serious problems.

U.S. Pat. Nos. 6,974,471, 2004/0073289, 7,318,835, 7,279,003 disclose prior art prostheses for implantation within a curved body lumen.

In general this application relates to the placement of prostheses in the aorta in the region known as the thoracic arch where the aorta leaves the heart and curves over in approximately a semi-circle to the descending aorta and then into the abdominal aorta and then into the lower limbs via the iliac arteries. The invention is, however, not so restricted and can relate to placement of prostheses within or in place of lumens in any portion of a human or animal body, though it is particularly relevant to curved lumens, particularly tightly curved lumens.

SUMMARY OF THE INVENTION

The present invention seeks to provide an improved introducer for deploying a stent graft within a curved lumen.

According to a first aspect of the present invention, there is provided an introducer for deploying a stent graft in a curved lumen, the introducer including: a carrier for a stent graft including a plurality of stents; a release mechanism including a constraining mechanism operable to maintain at least a portion of at least one stent of the stent graft in a radially constrained configuration during deployment whilst allowing at least a portion of the stent graft to expand, wherein the portion of the constrainable stent is radially constrained substantially entirely therearound; the release mechanism operable to enable the constrained stent to expand so as to overlap with the interior of at least a portion of an adjacent stent in the expanded portion of the stent graft.

The introducer enables a substantially cylindrical stent graft to be deployed in a curved lumen without the need to match the curve of the stent graft to the lumen either prior to, or during, deployment. Furthermore, the stent graft can be accommodated within a curved lumen without the stents bunching together and creating gaps that might cause blood leakage.

In a preferred embodiment, the constrainable stent is not the most proximal stent of the stent graft or the most distal stent of the stent graft. This assists in enabling the ends of the stent graft to be securely anchored within the vessel.

The constraining mechanism may include a release wire for co-operating with a wire-receiving mechanism provided on the constrainable stent.

More than one stent may be maintained in a constrained configuration during deployment whilst at least a portion of the stent graft expands.

According to another aspect of the present invention, there is provided a stent graft for deployment within a curved lumen by means of the above-described introducer, the stent graft including a plurality of stents, the stent graft including a mechanism for allowing at least a portion of at least one stent to be radially constrained during deployment whilst a portion of the stent graft is expanded, wherein the portion of the constrainable stent is radially constrained substantially entirely therearound.

The stent graft is typically substantially cylindrical prior to deployment, but is able to be securely located within a curved lumen, irrespective of the extent of the curvature of the lumen and without the need to match curvature of the stent graft with the curvature of the lumen either prior to, or during, deployment.

Preferably, the mechanism is not provided at the most proximal stent of the stent graft or at the most distal stent of the stent graft. This facilitates secure anchoring of the stent graft within the lumen.

The mechanism may include at least one wire-receiver for co-operating with a release wire of the introducer. The wire-receiver may be a loop of material, such as a loop of thread.

In an embodiment, the mechanism may be provided at only one end of the constrainable stent, for example, it may be provided only at the proximal end of the constrainable stent.

In another embodiment, the mechanism may be provided at both the proximal end and the distal end of the constrainable stent.

The stent graft may include more than one constrainable stent. In an embodiment, it may include at least one constrainable stent in which the mechanism is provided only at one of its ends, and at least one constrainable stent in which the mechanism is provided at both its proximal end and its distal end.

BRIEF DESCRIPTION OF THE DRAWINGS

Embodiments of the present invention are described below, by way of example only, with reference to the accompanying drawings, in which.

DETAILED DESCRIPTION

It is to be understood that the Figures are schematic and do not show the various components in their actual scale. In many instances, the Figures show scaled up components to assist the reader.

In this description, when referring to a deployment assembly, the term distal is used to refer to an end of a component which in use is furthest from the surgeon during the medical procedure, including within a patient. The term proximal is used to refer to an end of a component closest to the surgeon and in practice in or adjacent an external manipulation part of the deployment or treatment apparatus.

On the other hand, when referring to an implant such as a stent or stent graft, the term proximal refers to a location which in use is closest to the patient's heart, in the case of a vascular implant, and the term distal refers to a location furthest from the patient's heart.

Figure 1:
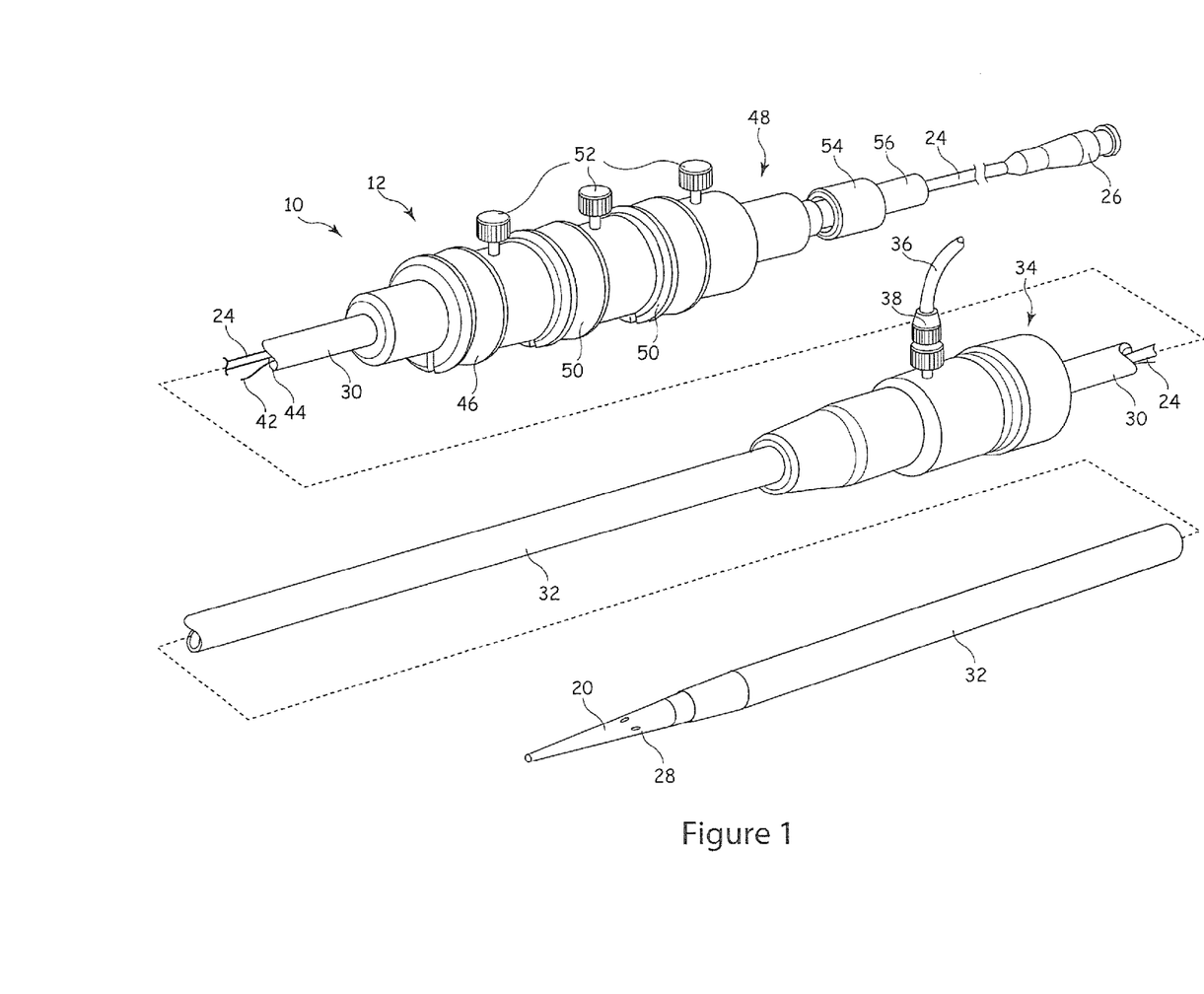
FIGS. 1 and 2 show an example of an implant deployment device.
Figure 2:
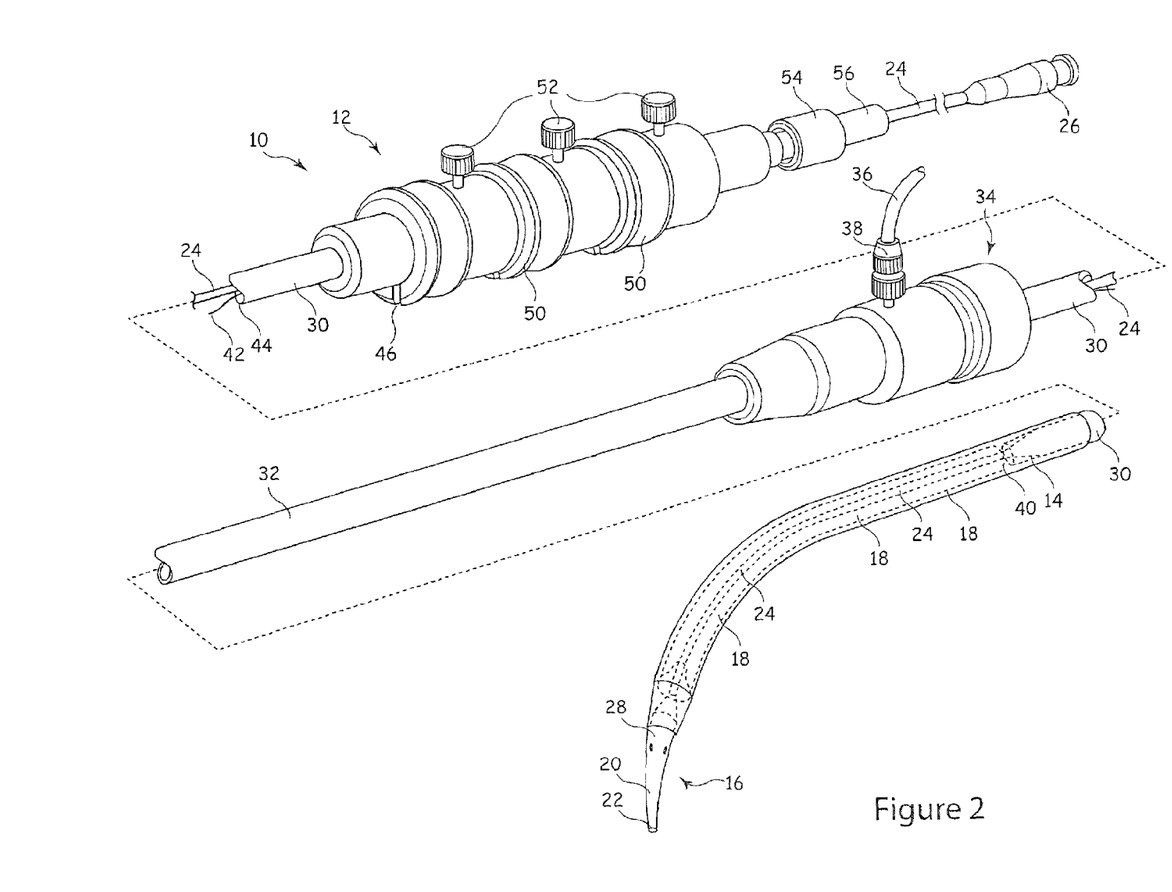

Referring to FIGS. 1 and 2, an implant deployment device 10 includes an external manipulation section 12, a proximal attachment region 14 and a distal attachment region 16. The proximal attachment region 14 and the distal attachment region 16 secure the two ends of the implant 18. During the medical procedure to deploy the implant 18, the proximal and distal attachment regions 14 and 16 will travel through the patient's vasculature, in this example, to a desired deployment site. The external manipulation section 12 at the proximal end of the implant deployment device 10, which is operated by a surgeon to manipulate the introducer, remains outside of the patient throughout the procedure.

The distal attachment region 16 of the implant deployment device 10 includes a dilator tip 20, which is typically provided with a bore 22 therein for receiving a guide wire (not shown) of conventional type. The longitudinal bore 22 also provides a channel for the introduction of medical reagents. For example, it may be desirable to supply a contrast agent to allow angiography to be performed during placement and deployment phases of the medical procedure.

An inner catheter or cannula 24, conventionally made from a flexible thin walled metal tube, is fastened to the dilator tip 20. The inner catheter 24 is flexible so that the implant deployment device 10 can be advanced along a relatively tortuous vessel, such as a femoral artery, and so that the distal end of the implant deployment device 10 can be longitudinally and rotationally manipulated. The inner catheter 24 carries a stent 18 or other device to be implanted in the patient. The catheter 24 extends through the implant deployment device 10 to the manipulation section 12, terminating at a connection device 26, in conventional manner.

The connection device 26 is designed to accept a syringe to facilitate the introduction of reagents into the inner catheter 24 and for this purpose is typically provided with a threaded luer lock connection.

Where provided, a pusher sheath or rod 30 (hereinafter referred to as a pusher member), typically made from a plastics material, is mounted coaxial with and radially outside of the inner catheter 24. The pusher member 30 is "thick walled", that is the thickness of its wall is preferably several times greater than that of the guide wire catheter 24. In some instances, the pusher member 30 and the inner catheter 24 are the same component, possibly having different outer diameters at the location at which the stent 18 is to be carried.

A sheath 32 extends coaxially over and radially outside of the pusher member 30. The pusher member 30 and the sheath 32 extend distally to the manipulation region 12.

The implant 18, which may be a stent, a stent graft or any other implant or prosthesis deliverable by the implant deployment device 10, is retained in a compressed condition by the sheath 32. The sheath 32 extends proximally to a sheath manipulator and haemostatic sealing unit 34 of the external manipulation section 12. The haemostatic sealing unit 34 includes a haemostatic seal (not shown) and a side tube 36 held to the unit 34 by a conventional luer lock 38.

The sheath manipulator and haemostatic sealing unit 34 also includes a clamping collar (not shown) that clamps the sheath 32 to the haemostatic seal and a silicone seal ring (not shown) that forms a haemostatic seal around the pusher member 30. The side tube 38 facilitates the introduction of medical fluids between the pusher member 30 and the sheath 32. Saline solution is typically used.

During assembly of the implant deployment device 10, the sheath 32 is advanced over the proximal end of the dilator tip 20 of the proximal attachment region 16 while the implant 18 is held in a compressed state by an external force. A suitable distal attachment (retention) section (not visible in this view) is coupled to the pusher member 30 and retains a distal end 40 of the prosthesis 18 during the procedure. The distal end of the prosthesis 18 may be provided with a loop of material (not shown) through which a distal restraining wire 42 extends. The distal restraining wire also extends through an aperture (not shown in FIGS. 1 and 2) in the proximal attachment section 40 into an annular region 44 between the inner catheter 24 and the pusher member 30. The distal restraining wire 42 extends through the annular space 44 to the manipulation region 12 and exits the annular space 44 at a distal wire release mechanism 46.

A proximal portion of the external manipulation section 12 includes at least one restraining wire actuation section 50 mounted on a body 48, in turn mounted onto the pusher member 30. The inner catheter 24 passes through the body 48. The distal wire release mechanism 46 and the proximal wire release mechanism 50 are mounted for slidable movement on the body 48.

Clamping screws 52 prevent inadvertent early release of the prosthesis 18. A haemostatic seal (not shown) is included so that the release wires can extend out through the body 48 without unnecessary blood loss during the medical procedure.

A proximal portion of the external manipulation section 12 includes a pin vice 54 mounted onto the proximal end of the body 48. The pin vice 54 has a screw cap 56. When screwed in, vice jaws (not shown) of the pin vice 54 clamp against or engage the inner catheter 24. When the vice jaws are engaged, the inner catheter 24 can only move with the body 48 and hence it can only move with the pusher member 30. With the screw cap 56 tightened, the entire assembly can be moved together as one piece.

Once the implant deployment device 10 is in the desired deployment position, the sheath 32 is withdrawn and the proximal and distal wire release mechanisms 50, 46 are released to allow the prosthesis 18 to expand.

For some procedures, the sheath 32 may be left in place after expansion of the implant 18. The pusher member 30 and inner catheter 24 may be withdrawn and replaced by a further component, using the sheath 32 as a guide.

Figure 3:
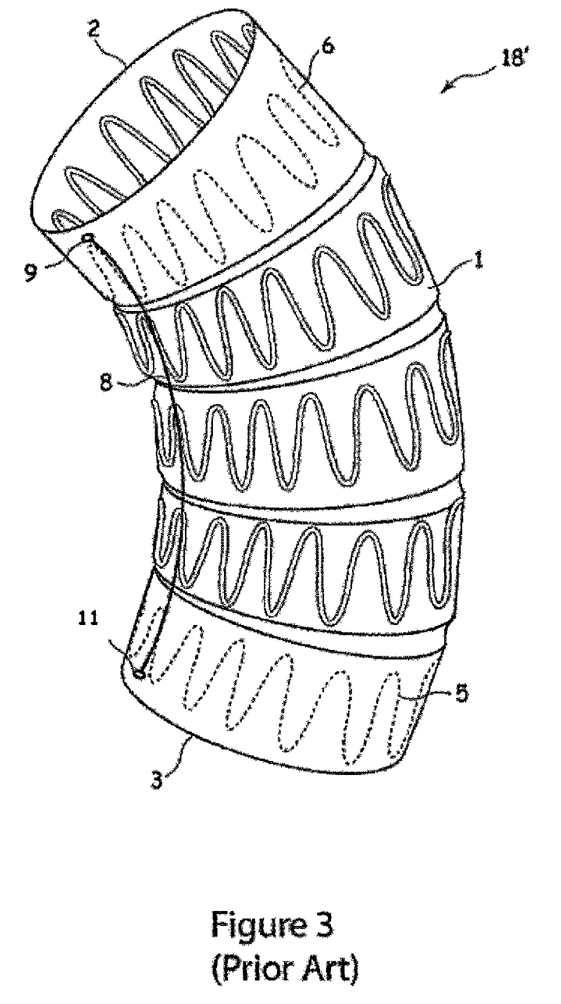
FIG. 3 shows a prior art stent graft for deployment in a curved lumen.

FIG. 3 illustrates a prior art stent graft 18' for deployment within a curved body lumen. The stent graft 18' comprises a graft material tube 1 which is substantially cylindrical. The graft material tube 1 has a proximal end 2 and a distal end 3. The graft 1 has a number of self expanding zig-zag or well-known Gianturco Z-stents 4 positioned at intervals along the length of the tube and providing the force necessary to open the graft 1 out to the walls of the aorta when deployed. The stents 5 and 6 at the distal end 3 and proximal end 2 respectively are inside the graft 1 and the other intermediate stents 4 are on the outside of the graft 1.

The stent graft 18' includes a length reduction arrangement comprising an elastic material 8 such as a silicone rubber or similar material which is fastened at 9 at the proximal end 2 of the prosthesis 18' and joined at 11 near the distal end 3 of the prosthesis 18'. The length reduction arrangement can also comprise a shape memory metal such as Nitinol, a nickel titanium alloy, which is heat set in a curved configuration.

Upon deployment, the ends of the graft 18' are released from a deployment device and the elastic material 8 takes up its shortened rest position so that the points 9 and 11 move closer together which causes the graft to form a curved shape. The curved stent graft 18' can then sit within a body lumen having the same curve.

Figure 4:
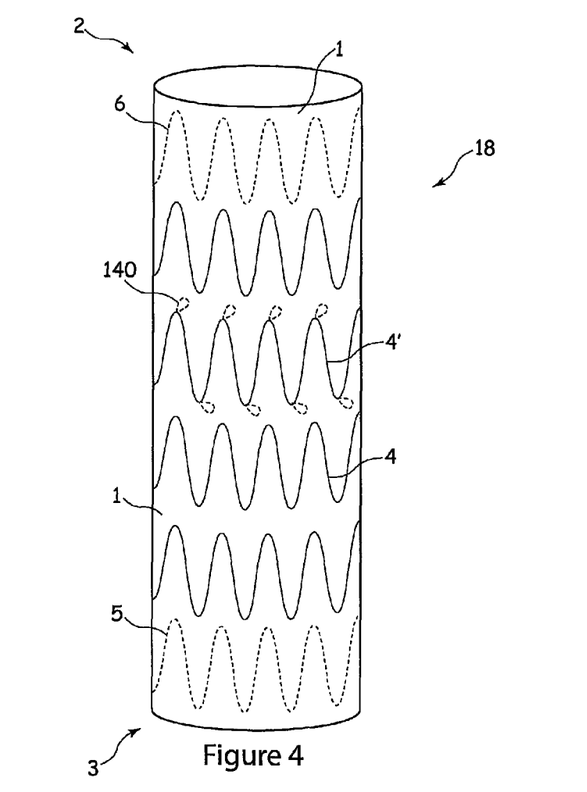
FIG. 4 shows a stent graft in accordance with an embodiment of the present invention.
Figure 5:
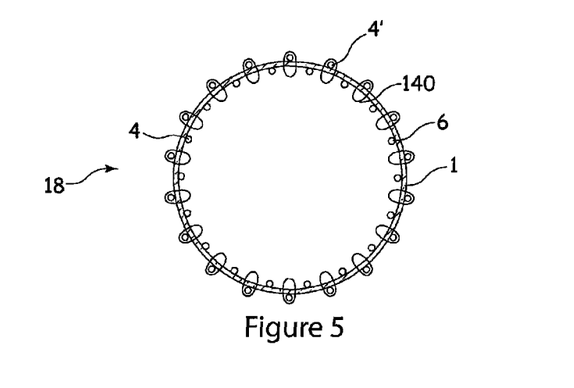
FIG. 5 shows an end view of the stent graft of FIG. 4.

FIGS. 4 and 5 illustrate a stent graft 18 in accordance with an embodiment of the present invention. The stent graft 18 is formed from a tubular piece of biocompatible graft material 1 having, in this example, six Z-stents 4, 4', 5, 6 disposed along its length. In this embodiment the stents 5, 6 found at the distal end 3 and the proximal end 2 of the tubular piece of graft material 1 are located on the inside of the tube 1, whereas the intermediate stents 4, 4' are located on the outside of the tube 1.

In this embodiment, one of the stents 4' is provided, at substantially equally spaced locations therearound, with loops of, in this embodiment, suture material 140. The loops of suture material 140 are able to engage with a release wire 42' of an introducer 10' for deployment of the stent graft 18. The purpose of this is described below.

Figure 6:
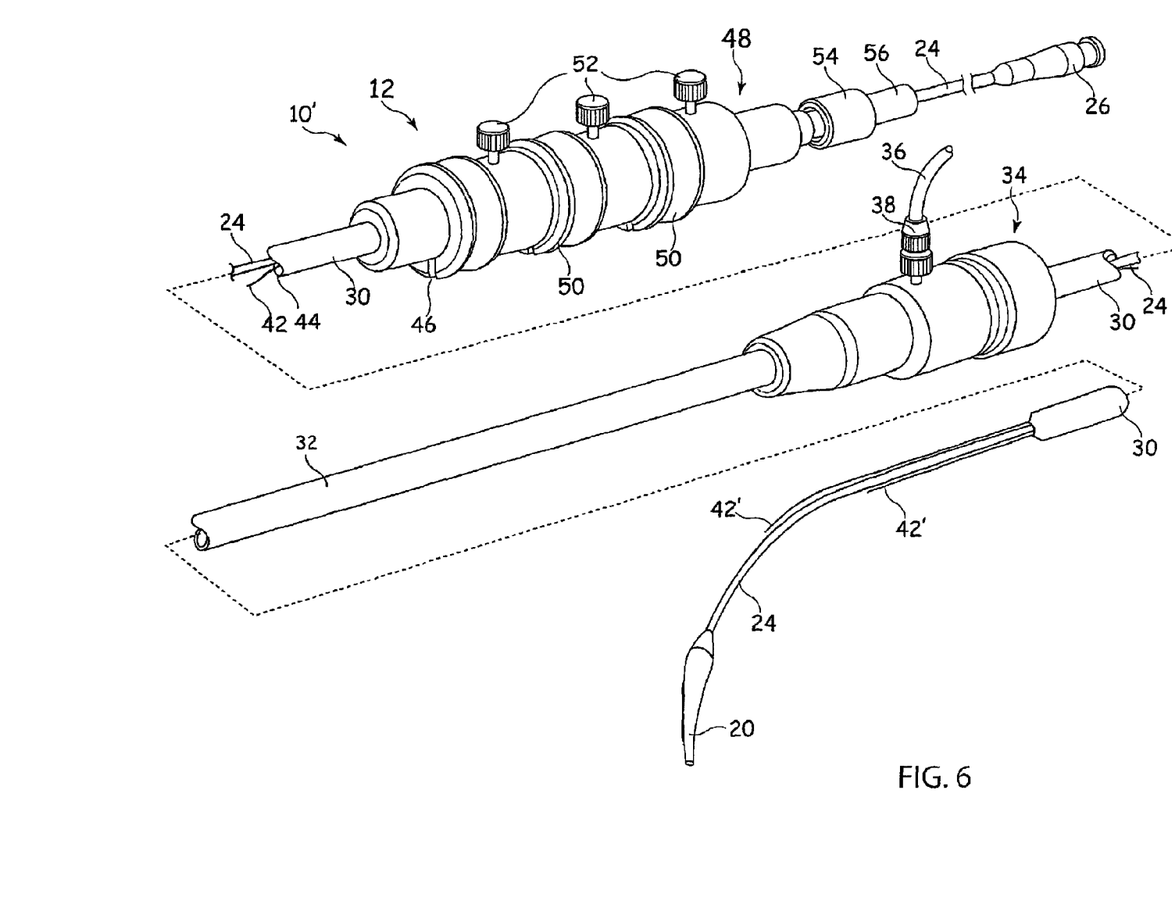
FIG. 6 shows an embodiment of an introducer for deploying the stent graft of FIG. 4.

For deployment of the stent graft 18 illustrated in FIGS. 4 and 5, the stent graft 18 is loaded in a radially compressed condition onto an inner catheter 24 of a deployment device 10' such as that shown in FIG. 6. The introducer 10' illustrated in FIG. 6 is similar to that shown in FIGS. 1 and 2. However, the introducer 10' shown in FIG. 6 includes a release mechanism including trigger wires 42' able to engage with the suture loops 140 of the stent graft 18. The compressed stent graft 18 is then covered by the sheath 32 in a conventional manner for deployment.

The stent graft 18 is delivered to the site of deployment, which in this example is within a curved body lumen (such as the thoracic arch). Once the implant deployment device 10 is in the desired deployment position, the sheath 32 is withdrawn and the stent graft 18 is allowed to expand (see FIG. 7). However, the engagement between the release wires 42 and the suture loops 140 retains a single stent 4' in a constrained configuration. The constrained stent 4' is typically constrained by over 50% of its expanded configuration, and may be constrained by up to 70 or 80%. This will depend upon the spacing between the stents. In practice it will be kept in its fully constrained condition, whereby it is constrained around the catheter 24 of the implant deployment device 10. In an embodiment, however, the constrained stent 4' may expand partially prior to release of the constraining mechanism. In a preferred embodiment the partial expansion comprises the constrained stent 4' expanding to no more than 50% of its fully deployed diameter.

Figure 7:
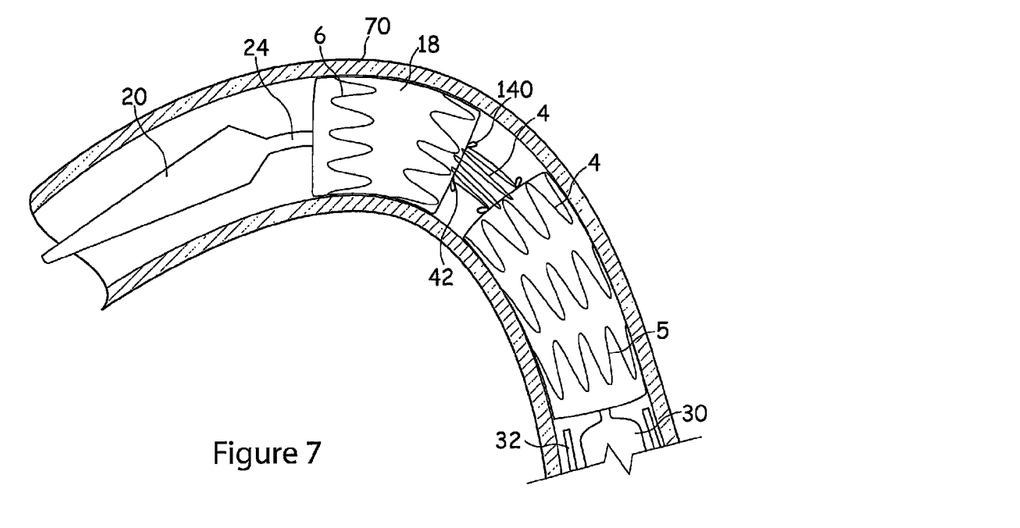
FIG. 7 shows deployment of the stent graft of FIG. 4 in a curved body lumen.

Next, the release wires 42' are released from the suture loops 140 to allow the constrained stent 4' to expand.

Figure 8:
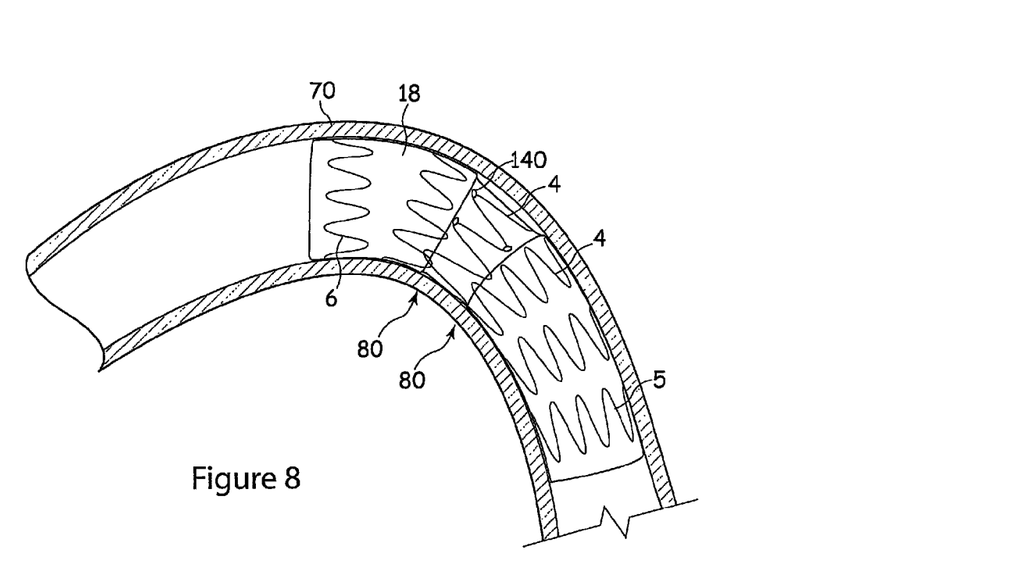
FIG. 8 shows the stent graft of FIG. 4 deployed in a curved body lumen.

Once the constrained stent 4' has expanded, the pusher member 30 and inner catheter 24 may be withdrawn leaving the expanded stent graft 18 in place (see FIG. 8).

FIGS. 7 and 8 illustrate the improved positioning effect of this deployment process. FIG. 7 shows the stent graft 18 partially expanded after withdrawal of the sheath 32. Only the constrained stent 4' remains in its compressed state by means of the release wires 42' and the suture loops 140. The stent graft 18 is located such that the constrained stent 4' is positioned at the tightest part of the bend of the curved body vessel 70. As such, the stents 4, 5, 6, which are allowed to expand as soon as the sheath 32 is withdrawn, engage against the walls of the body vessel 70 effectively because the vessel is not too curved at the location where the stents 4, 5, 6 of the expanded portion are located. It can be seen from FIG. 7, however, that the stent 4 located immediately proximally of the constrained 4' and the stent 4 located immediately distally of the constrained stent 4' are positioned such that they are closer together on the inside part of the curved body lumen 70 than they are towards the outside of the curve. This results from the constrained stent 4' drawing the graft material 1 and the adjacent stents 4 towards it. As a result, the adjacent stents 4 are able to locate within the vessel 70 closer together on the inside of the curve than they would have if the stent 4' between them had not been constrained whilst they expand. Consequently, when the constrained stent 4' is allowed to expand it overlaps 80 with its adjacent stents 4 on the inside of the curve of the curved body vessel 70. This is because the gap between the adjacent stents 4 is less than the length of the constrained stent 4'. Because the stents 4 adjacent to the constrained stent 4' were allowed to expand first, these properly engage the wall of the vessel 70, and the expanded constrained stent 4' engages with the interior of the adjacent stents 4 providing an area of overlap 80.

Figure 9:
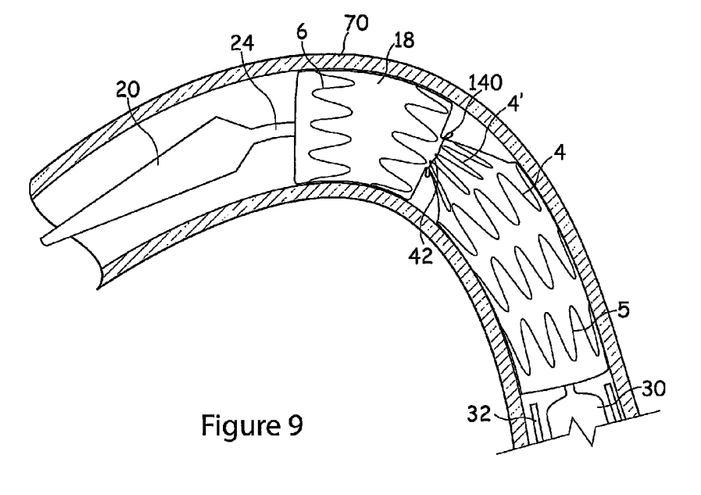
FIG. 9 shows deployment of another embodiment of a stent graft in a curved body lumen.
Figure 10:
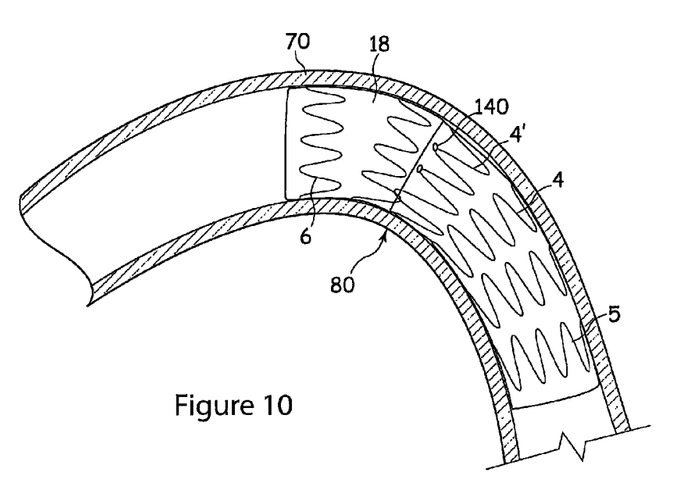
FIG. 10 shows the stent graft of FIG. 6 deployed in a curved body lumen.

A second embodiment is illustrated in FIGS. 9 and 10. The difference between the embodiment of FIGS. 9 and 10 and that of FIGS. 7 and 8 is that the constrained stent is constrained only at its proximal end so that it forms a "cone-shape" prior to release, but after expansion of the remainder of the stent graft 18. Again, when the constrained stent 4' is allowed to expand by removal of the release wire 42 from the suture loops 140, the constrained stent 4' expands such that it overlaps with the interior of the stent 4 immediately proximal to the constrained stent 4'. As shown in FIG. 10, the result is a single region of overlap 80 between the constrained stent 4' and its immediately proximal stent 4.

Constraining only the proximal end of the constrained stent 4' can provide a positioning of the stent graft 18 that maximises blood flow through the stent graft 18 after deployment.

Figure 11:
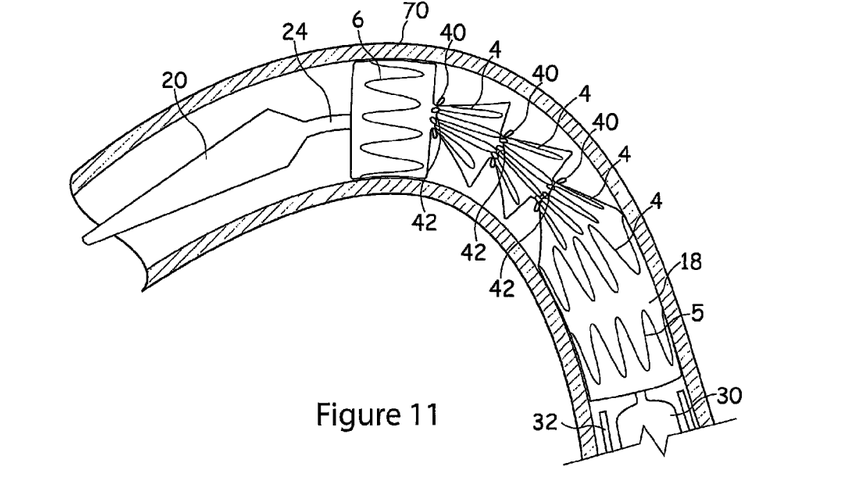
FIG. 11 shows deployment of another embodiment of a stent graft in a curved body lumen.
Figure 12:
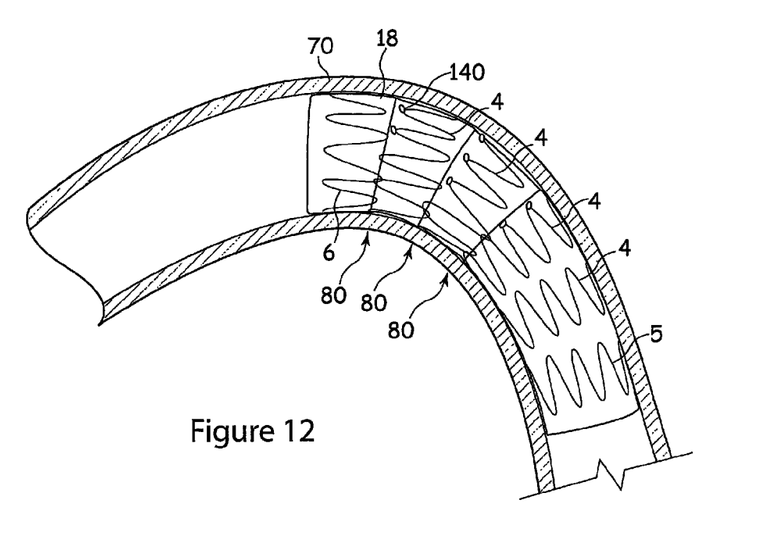
FIG. 12 shows the stent graft of FIG. 10 deployed in a curved body lumen.

In a third embodiment, more than one constrained stent 4' is provided with suture loops 140. In such an embodiment, each constrained stent 4' may include suture loops 140 at both its proximal ends and distal ends (c.f. FIG. 7), or, as illustrated in FIG. 11, (and in particular, where two adjacent constrained stents 4' are provided) each constrained stent 4' is provided with suture loops only at one end, in this example, the proximal ends. As illustrated in FIG. 12 this arrangement leads to a plurality of regions of overlap 80 with constrained stents 4' overlapping with the interior of an immediately proximal stent 4, 6.

An advantage of the above-described embodiments is that a substantially straight stent graft 18 can be deployed in a curved vessel. The stents 4 adjacent the constrained stent expand first and are properly anchored within the vessel. As the constrained stent 4' expands during a second stage of deployment, the stent graft 18 can be used in any type of vessel, whether straight, having only a slight bend, or having a sharp bend. Proper curvature of the stent graft 18 within the vessel is therefore obtained. In addition, the curve of the stent graft 18 does not have to be matched to the curve of the vessel prior to deployment. Furthermore, the surgeon or clinician does not have to ensure that the stent graft is deployed in a particular orientation to match the curve of the vessel as is the case with prior art prostheses. Constraining a stent 4' creates a neck portion, which imparts increased flexibility to the stent graft 18. This assists in enabling the stent graft 18 to conform to the curvature of a vessel 70 irrespective of the extent of the curvature of the vessel.

Of course, the skilled person will appreciate that the different types of constrained stent 4' may be combined within a single stent graft 18 where appropriate. Furthermore, the constrained stent 4' may be located at any point along the stent graft 18, depending on the particular requirements. For example, the constrained stent 4' may be at the proximal end, in the middle, or in any one or more of the stents along the stent graft 18. In another modification, it is envisaged that every stent of the stent graft 18 could be constrained, preferably only at one end, which would preferably be at the proximal end of each stent 4'. In an embodiment, the constrained stent 4' is not the stent 6 at the proximal end 2 of the stent graft 18. This is because the stent 6 at the proximal end 2 of the stent graft 18 can be useful for anchoring and positioning of the stent graft 18.

In another modification, the release wire 42' may be the same as the wire 42 that holds the proximal end of the stent graft to the distal end of the introducer.

In another modification, the suture loops 140 of different constrained stents 140 can co-operate with different release wires 42'. This enables greater control over the deployment process where desired by allowing different constrained stents 4' to be released in a particular desired order.

The suture loops 140 could be provided on the graft material 1 instead of on the stent 4'. The suture loops 140 could additionally or alternatively be provided to co-operate with release wires 42 inside the tubular graft 1 instead of outside.

Figure 13:
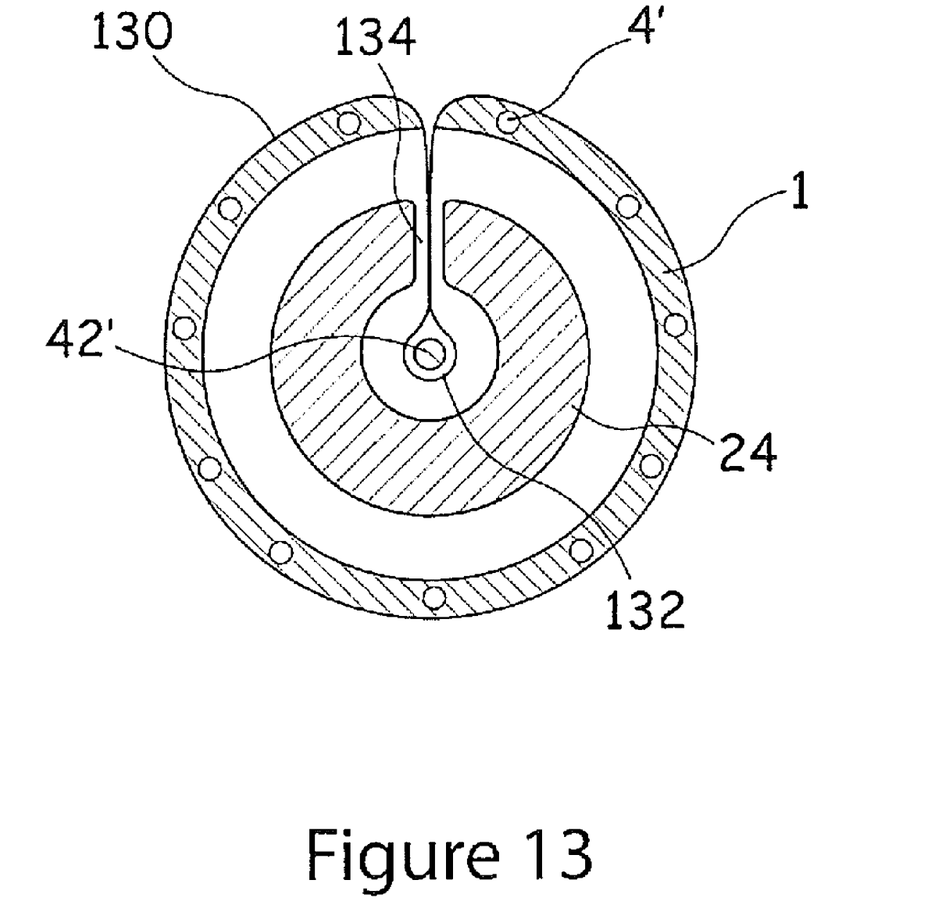
FIG. 13 illustrates one possible arrangement of a stent graft and an implant deployment device.

In another example of a restraining mechanism illustrated in FIG. 13, a thread of suture material 130 having loops 132 at each end may be provided around the stent 4' of the stent graft 18, and which, when pulled tight, constrains the stent 4'. The loops 132 at each end of the thread of suture material 130 overlap one another and a release wire 42' is threaded therethrough, thereby maintaining an overlap of the loops 132 and maintaining the stent 4' in its constrained configuration. Withdrawal of the release wire 42' allows the loops 132 at each end of the thread of suture material 130 to separate and the constrained stent 4' to expand. In the example illustrated in FIG. 13 the inner catheter 24 is provided with an aperture 134 through which the suture material 132 extends in order to engage with the release wire 42'. Other suitable arrangements may be envisaged.

The term thread as used herein is intended to include any filamentary material which can perform the stated function and could, for example, be of conventional suture material, a multi-filamentary structure formed of yarns for example and of a natural or synthetic material such as cotton, other biocompatible material or a polymer material such as polyester, or a mono-filamentary structure of a natural material, other biocompatible material, a metal such as gold or an alloy such as Nitinol.

The features of the various embodiments described above and their modifications may be substituted for or combined with one another as desired. It is also to be understood that the various features of the dependent claims appended hereto may be used with one another in any desired combination of those claims.

What is claimed is:

1. An introducer for deploying a stent graft in a curved lumen, the introducer including:
   a carrier for a stent graft;
   a withdrawable sheath for retaining a stent graft in a compressed condition;
   a release mechanism including a constraining mechanism, wherein the constraining mechanism includes at least one release wire;
   a substantially cylindrical stent graft, including a plurality of stents, mounted on the carrier, the stent graft including at least one wire-receiver co-operating with the at least one release wire of the release mechanism, wherein the at least one wire-receiver and the at least one release wire radially constrain at least a portion of at least one constrainable stent of the plurality of stents of the stent graft to form a constrained stent portion of a constrained stent that is radially constrained substantially entirely therearound, wherein at least an adjacent portion of an adjacent stent of the plurality of stents of the stent graft is not radially constrained by the at least one release wire and forms an expanded portion of the stent graft when not compressed by the sheath whilst the constrained stent portion is simultaneously maintained in its radially constrained configuration by the at least one wire-receiver and the at least one release wire, wherein at least the most proximal stent of the stent graft and at least the most distal stent of the stent graft are not constrained by the at least one wire-receiver and the at least one release wire while the constrained stent portion is maintained in its radially constrained configuration;

the at least one release wire and the at least one wire-receiver together being releasable to enable the constrained stent portion to expand so as to overlap with the interior of the adjacent portion of the adjacent stent in an the expanded portion of the stent graft, thereby to enable the stent graft to be deployed in a curved lumen without the need to match the curve of the stent graft to the lumen either prior to, or during deployment.

2. An introducer as claimed in claim 1, wherein at least a portion of more than one stent is constrained by the at least one wire-receiver and the at least one release wire.

3. An introducer as claimed in claim 1, wherein the at least one wire-receiver is a loop of material.

4. An introducer as claimed in claim 3, wherein the loop of material is a thread.

5. An introducer as claimed in claim 1, wherein the at least one wire-receiver is provided only at one end of the constrained stent, and wherein another end of the constrained stent is not provided with any wire-receiver.

6. An introducer as claimed in claim 1, wherein the at least one wire-receiver is provided at both a proximal end and a distal end of the constrained stent.

7. An introducer claimed in claim 1, wherein more than one stent of the stent graft is constrained.

8. An introducer as claimed in claim 7, including at least one constrained stent in which a wire-receiver is provided only at one of its ends and at least one constrained stent in which a wire-receiver is provided at both its proximal end and its distal end.

* * * * *

UNITED STATES PATENT AND TRADEMARK OFFICE
CERTIFICATE OF CORRECTION

PATENT NO.         : 8,480,725 B2                            Page 1 of 1
APPLICATION NO.    : 12/609553
DATED              : July 9, 2013
INVENTOR(S)        : Erik E. Rasmussen et al.

It is certified that error appears in the above-identified patent and that said Letters Patent is hereby corrected as shown below:

In the Claims

In column 9, claim 1, line 6, after "of the adjacent stent in" delete "an".

Signed and Sealed this
Tenth Day of September, 2013

Teresa Stanek Rea
*Acting Director of the United States Patent and Trademark Office*